United States Patent
Kreuzaler et al.

(10) Patent No.: US 9,371,538 B2
(45) Date of Patent: Jun. 21, 2016

(54) METHOD FOR INCREASING PHOTOSYNTHETIC CARBON FIXATION USING GLYCOLATE DEHYDROGENASE MULTI-SUBUNIT FUSION PROTEIN

(75) Inventors: Fritz Kreuzaler, Aachen (DE); Greta Noelke, Aachen (DE); Christoph Peterhaensel, Hannover (DE); Stefan Schillberg, Aachen (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 743 days.

(21) Appl. No.: 13/577,064

(22) PCT Filed: Feb. 3, 2011

(86) PCT No.: PCT/EP2011/051505
§ 371 (c)(1),
(2), (4) Date: Aug. 3, 2012

(87) PCT Pub. No.: WO2011/095528
PCT Pub. Date: Aug. 11, 2011

(65) Prior Publication Data
US 2012/0317683 A1    Dec. 13, 2012

Related U.S. Application Data

(60) Provisional application No. 61/368,012, filed on Jul. 27, 2010.

(30) Foreign Application Priority Data

Feb. 4, 2010   (EP) .................................. 10152714

(51) Int. Cl.
*C12N 15/82*    (2006.01)
*C12N 9/04*    (2006.01)

(52) U.S. Cl.
CPC .......... *C12N 15/8269* (2013.01); *C12N 9/0006* (2013.01); *C12N 15/8261* (2013.01)

(58) Field of Classification Search
None
See application file for complete search history.

(56) References Cited

U.S. PATENT DOCUMENTS 7,208,318 B2 *   4/2007   Hain et al. .................... 435/468

FOREIGN PATENT DOCUMENTS

| EP | 1367127 A1 | 12/2003 |
|---|---|---|
| WO | WO 00/26390 | 5/2000 |
| WO | WO-2010012796 A1 | 2/2010 |

OTHER PUBLICATIONS

Kebeish, R. et al. Nature Biotechnology (May 5, 2007) vol. 25, pp. 593-599.*
Khan, M. TRENDS in Biotechnology; vol. 25, No. 10 pp. 437-440.*
Wriggers, W. et al. Biopolymers (Peptide Science) 2005; vol. 80, pp. 736-746.*
Valentin, H. et al., "PHA production, from bacteria to plants", International Journal of Biological Macromolecules, vol. 25, pp. 303-306, 1999.
Kebeish, R. et al. "Chloroplastic photorespiratory bypass increases photosynthesis and biomass production in Arabidopsis thaliana" Nature Biotechnology, vol. 25, No. 5, Apr. 15, 1997.
Garg, A.K. et al., "Trehalose accumulation in rice plants confers high tolerance levels to different abiotic stresses", Proceedings of the National Academy of Sciences of USA, vol. 99, No. 25, Dec. 10, 2002.
Khan et al., "Engineering photorespiration in chloroplasts: a novel strategy for increasing biomass production", Trends in Biotechnology, vol. 25, No. 10, Sep. 26, 2007.
Ralley, L. et al., "Metabolic Engineering of Ketocarotenoid Formation in Higher Plants." *The Plant Journal* 39, 477-486 (2004).

* cited by examiner

*Primary Examiner* — Russell Kallis
(74) *Attorney, Agent, or Firm* — Arent Fox LLP

(57) ABSTRACT

The invention relates to a method for stimulating the growth of the plants and/or improving the biomass production and/or increasing the carbon fixation by the plant comprising introducing into a plant cell, plant tissue or plant one or more nucleic acids, wherein the introduction of the nucleic acid(s) results inside the chloroplast of a de novo expression of one or more polypeptides having the enzymatic activity of a glycolate dehydrogenase made up from translationally fused subunits of bacterial multi-subunit glycolate dehydrogenase enzymes.

21 Claims, 2 Drawing Sheets

A

B

Figure 1:
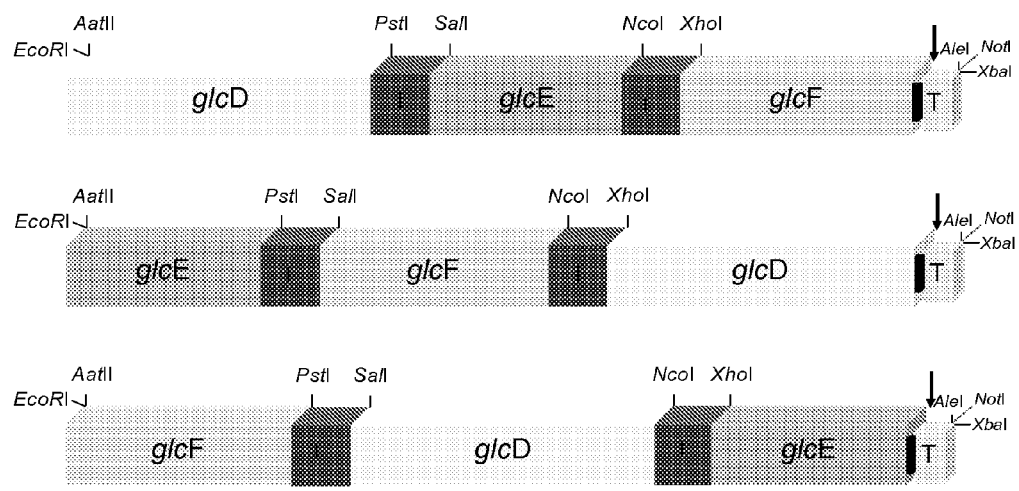

SEQUENCE LISTING

```
<160> NUMBER OF SEQ ID NOS: 6

<210> SEQ ID NO 1
<211> LENGTH: 1500
<212> TYPE: DNA
<213> ORGANISM: Escherichia coli
<220> FEATURE:
<221> NAME/KEY: CDS
<222> LOCATION: (1)..(1497)
<223> OTHER INFORMATION: gcl D

<400> SEQUENCE: 1 atg agc atc ttg tac gaa gag cgt ctt gat ggc gct tta ccc gat gtc      48
Met Ser Ile Leu Tyr Glu Glu Arg Leu Asp Gly Ala Leu Pro Asp Val
1               5                   10                  15 gac cgc aca tcg gta ctg atg gca ctg cgt gag cat gtc cct gga ctt      96
Asp Arg Thr Ser Val Leu Met Ala Leu Arg Glu His Val Pro Gly Leu
                20                  25                  30 gag atc ctg cat acc gat gag gag atc att cct tac gag tgt gac ggg     144
Glu Ile Leu His Thr Asp Glu Glu Ile Ile Pro Tyr Glu Cys Asp Gly
            35                  40                  45 ttg agc gcg tat cgc acg cgt cca tta ctg gtt gtt ctg cct aag caa     192
Leu Ser Ala Tyr Arg Thr Arg Pro Leu Leu Val Val Leu Pro Lys Gln
        50                  55                  60 atg gaa cag gtg aca gcg att ctg gct gtc tgc cat cgc ctg cgt gta     240
Met Glu Gln Val Thr Ala Ile Leu Ala Val Cys His Arg Leu Arg Val
65                  70                  75                  80 ccg gtg gtg acc cgt ggt gca ggc acc ggg ctt tct ggt ggc gcg ctg     288
Pro Val Val Thr Arg Gly Ala Gly Thr Gly Leu Ser Gly Gly Ala Leu
                85                  90                  95 ccg ctg gaa aaa ggt gtg ttg ttg gtg atg gcg cgc ttt aaa gag atc     336
Pro Leu Glu Lys Gly Val Leu Leu Val Met Ala Arg Phe Lys Glu Ile
                100                 105                 110 ctc gac att aac ccc gtt ggt cgc cgc gcg cgc gtg cag cca ggc gtg     384
Leu Asp Ile Asn Pro Val Gly Arg Arg Ala Arg Val Gln Pro Gly Val
            115                 120                 125 cgt aac ctg gcg atc tcc cag gcc gtt gca ccg cat aat ctc tac tac     432
Arg Asn Leu Ala Ile Ser Gln Ala Val Ala Pro His Asn Leu Tyr Tyr
```

-continued

|     |     |     |     | 130 |     |     |     | 135 |     |     |     | 140 |     |     |     |      |
|---|---|---|---|---|---|---|---|---|---|---|---|---|---|---|---|---|
| gca | ccg | gac | cct | tcc | tca | caa | atc | gcc | tgt | tcc | att | ggc | ggc | aat | gtg | 480 |
| Ala | Pro | Asp | Pro | Ser | Ser | Gln | Ile | Ala | Cys | Ser | Ile | Gly | Gly | Asn | Val |     |
| 145 |     |     |     | 150 |     |     |     | 155 |     |     |     | 160 |     |     |     |     |

| gct | gaa | aat | gcc | ggc | ggc | gtc | cac | tgc | ctg | aaa | tat | ggt | ctg | acc | gta | 528 |
|---|---|---|---|---|---|---|---|---|---|---|---|---|---|---|---|---|
| Ala | Glu | Asn | Ala | Gly | Gly | Val | His | Cys | Leu | Lys | Tyr | Gly | Leu | Thr | Val |     |
|     |     |     |     | 165 |     |     |     | 170 |     |     |     | 175 |     |     |     |     |

| cat | aac | ctg | ctg | aaa | att | gaa | gtg | caa | acg | ctg | gac | ggc | gag | gca | ctg | 576 |
|---|---|---|---|---|---|---|---|---|---|---|---|---|---|---|---|---|
| His | Asn | Leu | Leu | Lys | Ile | Glu | Val | Gln | Thr | Leu | Asp | Gly | Glu | Ala | Leu |     |
|     |     |     | 180 |     |     |     | 185 |     |     |     | 190 |     |     |     |     |     |

| aca | ctt | gga | tcg | gac | gcg | ctg | gat | tca | cct | ggt | ttt | gac | ctg | ctg | gcg | 624 |
|---|---|---|---|---|---|---|---|---|---|---|---|---|---|---|---|---|
| Thr | Leu | Gly | Ser | Asp | Ala | Leu | Asp | Ser | Pro | Gly | Phe | Asp | Leu | Leu | Ala |     |
|     |     | 195 |     |     |     | 200 |     |     |     | 205 |     |     |     |     |     |     |

| ctg | ttc | acc | gga | tcg | gaa | ggt | atg | ctc | ggc | gtg | acc | acc | gaa | gtg | acg | 672 |
|---|---|---|---|---|---|---|---|---|---|---|---|---|---|---|---|---|
| Leu | Phe | Thr | Gly | Ser | Glu | Gly | Met | Leu | Gly | Val | Thr | Thr | Glu | Val | Thr |     |
|     | 210 |     |     |     | 215 |     |     |     | 220 |     |     |     |     |     |     |     |

| gta | aaa | ctg | ctg | ccg | aag | ccc | ccc | gtg | gcg | cgg | gtt | ctg | tta | gcc | agc | 720 |
|---|---|---|---|---|---|---|---|---|---|---|---|---|---|---|---|---|
| Val | Lys | Leu | Leu | Pro | Lys | Pro | Pro | Val | Ala | Arg | Val | Leu | Leu | Ala | Ser |     |
| 225 |     |     |     | 230 |     |     |     | 235 |     |     |     | 240 |     |     |     |     |

| ttt | gac | tcg | gta | gaa | aaa | gcc | gga | ctt | gcg | gtt | ggt | gac | atc | atc | gcc | 768 |
|---|---|---|---|---|---|---|---|---|---|---|---|---|---|---|---|---|
| Phe | Asp | Ser | Val | Glu | Lys | Ala | Gly | Leu | Ala | Val | Gly | Asp | Ile | Ile | Ala |     |
|     |     |     | 245 |     |     |     | 250 |     |     |     | 255 |     |     |     |     |     |

| aat | ggc | att | atc | ccc | ggc | ggg | ctg | gag | atg | atg | gat | aac | ctg | tcg | atc | 816 |
|---|---|---|---|---|---|---|---|---|---|---|---|---|---|---|---|---|
| Asn | Gly | Ile | Ile | Pro | Gly | Gly | Leu | Glu | Met | Met | Asp | Asn | Leu | Ser | Ile |     |
|     |     |     | 260 |     |     |     | 265 |     |     |     | 270 |     |     |     |     |     |

| cgc | gcg | gcg | gaa | gat | ttt | att | cat | gcc | ggt | tat | ccc | gtc | gac | gcc | gaa | 864 |
|---|---|---|---|---|---|---|---|---|---|---|---|---|---|---|---|---|
| Arg | Ala | Ala | Glu | Asp | Phe | Ile | His | Ala | Gly | Tyr | Pro | Val | Asp | Ala | Glu |     |
|     |     | 275 |     |     |     | 280 |     |     |     | 285 |     |     |     |     |     |     |

| gcg | att | ttg | tta | tgc | gag | ctg | gac | ggc | gtg | gag | tct | gac | gta | cag | gaa | 912 |
|---|---|---|---|---|---|---|---|---|---|---|---|---|---|---|---|---|
| Ala | Ile | Leu | Leu | Cys | Glu | Leu | Asp | Gly | Val | Glu | Ser | Asp | Val | Gln | Glu |     |
|     | 290 |     |     |     | 295 |     |     |     | 300 |     |     |     |     |     |     |     |

| gac | tgc | gag | cgg | gtt | aac | gac | atc | ttg | ttg | aaa | gcg | ggc | gcg | act | gac | 960 |
|---|---|---|---|---|---|---|---|---|---|---|---|---|---|---|---|---|
| Asp | Cys | Glu | Arg | Val | Asn | Asp | Ile | Leu | Leu | Lys | Ala | Gly | Ala | Thr | Asp |     |
| 305 |     |     |     | 310 |     |     |     | 315 |     |     |     | 320 |     |     |     |     |

| gtc | cgt | ctg | gca | cag | gac | gaa | gca | gag | cgc | gta | cgt | ttc | tgg | gcc | ggt | 1008 |
|---|---|---|---|---|---|---|---|---|---|---|---|---|---|---|---|---|
| Val | Arg | Leu | Ala | Gln | Asp | Glu | Ala | Glu | Arg | Val | Arg | Phe | Trp | Ala | Gly |     |
|     |     |     | 325 |     |     |     | 330 |     |     |     | 335 |     |     |     |     |     |

| cgc | aaa | aat | gcg | ttc | ccg | gcg | gta | gga | cgt | atc | tcc | ccg | gat | tac | tac | 1056 |
|---|---|---|---|---|---|---|---|---|---|---|---|---|---|---|---|---|
| Arg | Lys | Asn | Ala | Phe | Pro | Ala | Val | Gly | Arg | Ile | Ser | Pro | Asp | Tyr | Tyr |     |
|     |     |     | 340 |     |     |     | 345 |     |     |     | 350 |     |     |     |     |     |

| tgc | atg | gat | ggc | acc | atc | ccg | cgt | cgc | gcc | ctg | cct | ggc | gta | ctg | gaa | 1104 |
|---|---|---|---|---|---|---|---|---|---|---|---|---|---|---|---|---|
| Cys | Met | Asp | Gly | Thr | Ile | Pro | Arg | Arg | Ala | Leu | Pro | Gly | Val | Leu | Glu |     |
|     |     | 355 |     |     |     | 360 |     |     |     | 365 |     |     |     |     |     |     |

| ggc | att | gcc | cgt | tta | tcg | cag | caa | tat | gat | tta | cgt | gtt | gcc | aac | gtc | 1152 |
|---|---|---|---|---|---|---|---|---|---|---|---|---|---|---|---|---|
| Gly | Ile | Ala | Arg | Leu | Ser | Gln | Gln | Tyr | Asp | Leu | Arg | Val | Ala | Asn | Val |     |
|     | 370 |     |     |     | 375 |     |     |     | 380 |     |     |     |     |     |     |     |

| ttt | cat | gcc | gga | gat | ggc | aac | atg | cac | ccg | tta | atc | ctt | ttc | gat | gcc | 1200 |
|---|---|---|---|---|---|---|---|---|---|---|---|---|---|---|---|---|
| Phe | His | Ala | Gly | Asp | Gly | Asn | Met | His | Pro | Leu | Ile | Leu | Phe | Asp | Ala |     |
| 385 |     |     |     | 390 |     |     |     | 395 |     |     |     | 400 |     |     |     |     |

| aac | gaa | ccc | ggt | gaa | ttt | gcc | cgc | gcg | gaa | gag | ctg | ggc | ggg | aag | atc | 1248 |
|---|---|---|---|---|---|---|---|---|---|---|---|---|---|---|---|---|
| Asn | Glu | Pro | Gly | Glu | Phe | Ala | Arg | Ala | Glu | Glu | Leu | Gly | Gly | Lys | Ile |     |
|     |     |     | 405 |     |     |     | 410 |     |     |     | 415 |     |     |     |     |     |

| ctc | gaa | ctc | tgc | gtt | gaa | gtt | ggc | ggc | agc | atc | agt | ggc | gaa | cat | ggc | 1296 |
|---|---|---|---|---|---|---|---|---|---|---|---|---|---|---|---|---|
| Leu | Glu | Leu | Cys | Val | Glu | Val | Gly | Gly | Ser | Ile | Ser | Gly | Glu | His | Gly |     |
|     |     | 420 |     |     |     | 425 |     |     |     | 430 |     |     |     |     |     |     |

| atc | ggg | cga | gaa | aaa | atc | aat | caa | atg | tgc | gcc | cag | ttc | aac | agc | gat | 1344 |
|---|---|---|---|---|---|---|---|---|---|---|---|---|---|---|---|---|
| Ile | Gly | Arg | Glu | Lys | Ile | Asn | Gln | Met | Cys | Ala | Gln | Phe | Asn | Ser | Asp |     |
|     | 435 |     |     |     | 440 |     |     |     | 445 |     |     |     |     |     |     |     |

| gaa | atc | acg | acc | ttc | cat | gcg | gtc | aag | gcg | gcg | ttt | gac | ccc | gat | ggt | 1392 |
|---|---|---|---|---|---|---|---|---|---|---|---|---|---|---|---|---|

```
Glu Ile Thr Thr Phe His Ala Val Lys Ala Ala Phe Asp Pro Asp Gly
    450                 455                 460 ttg ctg aac cct ggg aaa aac att ccc acg cta cac cgc tgt gct gaa    1440
Leu Leu Asn Pro Gly Lys Asn Ile Pro Thr Leu His Arg Cys Ala Glu
465                 470                 475                 480 ttt ggt gcc atg cat gtg cat cac ggt cat tta cct ttc cct gaa ctg    1488
Phe Gly Ala Met His Val His His Gly His Leu Pro Phe Pro Glu Leu
                485                 490                 495 gag cgt ttc tga                                                     1500
Glu Arg Phe <210> SEQ ID NO 2
<211> LENGTH: 499
<212> TYPE: PRT
<213> ORGANISM: Escherichia coli

<400> SEQUENCE: 2

Met Ser Ile Leu Tyr Glu Glu Arg Leu Asp Gly Ala Leu Pro Asp Val
1               5                   10                  15

Asp Arg Thr Ser Val Leu Met Ala Leu Arg Glu His Val Pro Gly Leu
            20                  25                  30

Glu Ile Leu His Thr Asp Glu Glu Ile Ile Pro Tyr Glu Cys Asp Gly
        35                  40                  45

Leu Ser Ala Tyr Arg Thr Arg Pro Leu Leu Val Val Leu Pro Lys Gln
    50                  55                  60

Met Glu Gln Val Thr Ala Ile Leu Ala Val Cys His Arg Leu Arg Val
65                  70                  75                  80

Pro Val Val Thr Arg Gly Ala Gly Thr Gly Leu Ser Gly Gly Ala Leu
                85                  90                  95

Pro Leu Glu Lys Gly Val Leu Leu Val Met Ala Arg Phe Lys Glu Ile
            100                 105                 110

Leu Asp Ile Asn Pro Val Gly Arg Arg Ala Arg Val Gln Pro Gly Val
        115                 120                 125

Arg Asn Leu Ala Ile Ser Gln Ala Val Ala Pro His Asn Leu Tyr Tyr
    130                 135                 140

Ala Pro Asp Pro Ser Ser Gln Ile Ala Cys Ser Ile Gly Gly Asn Val
145                 150                 155                 160

Ala Glu Asn Ala Gly Gly Val His Cys Leu Lys Tyr Gly Leu Thr Val
                165                 170                 175

His Asn Leu Leu Lys Ile Glu Val Gln Thr Leu Asp Gly Glu Ala Leu
            180                 185                 190

Thr Leu Gly Ser Asp Ala Leu Asp Ser Pro Gly Phe Asp Leu Leu Ala
        195                 200                 205

Leu Phe Thr Gly Ser Glu Gly Met Leu Gly Val Thr Thr Glu Val Thr
    210                 215                 220

Val Lys Leu Leu Pro Lys Pro Val Ala Arg Val Leu Leu Ala Ser Phe
225                 230                 235                 240

Phe Asp Ser Val Glu Lys Ala Gly Leu Ala Val Gly Asp Ile Ile Ala
                245                 250                 255

Asn Gly Ile Ile Pro Gly Gly Leu Glu Met Met Asp Asn Leu Ser Ile
            260                 265                 270

Arg Ala Ala Glu Asp Phe Ile His Ala Gly Tyr Pro Val Asp Ala Glu
        275                 280                 285

Ala Ile Leu Leu Cys Glu Leu Asp Gly Val Glu Ser Asp Val Gln Glu
    290                 295                 300
```

```
Asp Cys Glu Arg Val Asn Asp Ile Leu Leu Lys Ala Gly Ala Thr Asp
305                 310                 315                 320

Val Arg Leu Ala Gln Asp Glu Ala Glu Arg Val Arg Phe Trp Ala Gly
            325                 330                 335

Arg Lys Asn Ala Phe Pro Ala Val Gly Arg Ile Ser Pro Asp Tyr Tyr
        340                 345                 350

Cys Met Asp Gly Thr Ile Pro Arg Arg Ala Leu Pro Gly Val Leu Glu
    355                 360                 365

Gly Ile Ala Arg Leu Ser Gln Gln Tyr Asp Leu Arg Val Ala Asn Val
370                 375                 380

Phe His Ala Gly Asp Gly Asn Met His Pro Leu Ile Leu Phe Asp Ala
385                 390                 395                 400

Asn Glu Pro Gly Glu Phe Ala Arg Ala Glu Leu Gly Gly Lys Ile
            405                 410                 415

Leu Glu Leu Cys Val Glu Val Gly Gly Ser Ile Ser Gly Glu His Gly
                420                 425                 430

Ile Gly Arg Glu Lys Ile Asn Gln Met Cys Ala Gln Phe Asn Ser Asp
            435                 440                 445

Glu Ile Thr Thr Phe His Ala Val Lys Ala Ala Phe Asp Pro Asp Gly
    450                 455                 460

Leu Leu Asn Pro Gly Lys Asn Ile Pro Thr Leu His Arg Cys Ala Glu
465                 470                 475                 480

Phe Gly Ala Met His Val His His Gly His Leu Pro Phe Pro Glu Leu
                485                 490                 495

Glu Arg Phe

<210> SEQ ID NO 3
<211> LENGTH: 1053
<212> TYPE: DNA
<213> ORGANISM: Escherichia coli
<220> FEATURE:
<221> NAME/KEY: CDS
<222> LOCATION: (1)..(1050)
<223> OTHER INFORMATION: gcl E

<400> SEQUENCE: 3 atg cta cgc gag tgt gat tac agc cag gcg ctg ctg gag cag gtg aat      48
Met Leu Arg Glu Cys Asp Tyr Ser Gln Ala Leu Leu Glu Gln Val Asn
1               5                   10                  15 cag gcg att agc gat aaa acg ccg ctg gtg att cag ggc agc aat agc      96
Gln Ala Ile Ser Asp Lys Thr Pro Leu Val Ile Gln Gly Ser Asn Ser
                20                  25                  30 aaa gcc ttt tta ggt cgc cct gtc acc ggg caa acg ctg gat gtt cgt     144
Lys Ala Phe Leu Gly Arg Pro Val Thr Gly Gln Thr Leu Asp Val Arg
            35                  40                  45 tgt cat cgc ggc att gtt aat tac gac ccg acc gag ctg gtg ata acc     192
Cys His Arg Gly Ile Val Asn Tyr Asp Pro Thr Glu Leu Val Ile Thr
        50                  55                  60 gcg cgt gtc gga acg ccg ctg gtg aca att gaa gcg gcg ctg gaa agc     240
Ala Arg Val Gly Thr Pro Leu Val Thr Ile Glu Ala Ala Leu Glu Ser
65                  70                  75                  80 gcg ggg caa atg ctc ccc tgt gag ccg ccg cat tat ggt gaa gaa gcc     288
Ala Gly Gln Met Leu Pro Cys Glu Pro Pro His Tyr Gly Glu Glu Ala
                85                  90                  95 acc tgg ggc ggg atg gtc gcc tgc ggg ctg gcg ggg ccg cgt cgc ccg     336
Thr Trp Gly Gly Met Val Ala Cys Gly Leu Ala Gly Pro Arg Arg Pro
            100                 105                 110 tgg agc ggt tcg gtc cgc gat ttt gtc ctc ggc acg cgc atc att acc     384
Trp Ser Gly Ser Val Arg Asp Phe Val Leu Gly Thr Arg Ile Ile Thr
```

```
Trp Ser Gly Ser Val Arg Asp Phe Val Leu Gly Thr Arg Ile Ile Thr
        115                 120                 125 ggc gct gga aaa cat ctg cgt ttt ggt ggc gaa gtg atg aaa aac gtt    432
Gly Ala Gly Lys His Leu Arg Phe Gly Gly Glu Val Met Lys Asn Val
130                 135                 140 gcc gga tac gat ctc tca cgg tta atg gtc gga agc tac ggt tgt ctt    480
Ala Gly Tyr Asp Leu Ser Arg Leu Met Val Gly Ser Tyr Gly Cys Leu
145                 150                 155                 160 ggc gtg ctc act gaa atc tca atg aaa gtg tta ccg cga ccg cgc gcc    528
Gly Val Leu Thr Glu Ile Ser Met Lys Val Leu Pro Arg Pro Arg Ala
            165                 170                 175 tcc ctg agc ctg cgt cgg gaa atc agc ctg caa gaa gcc atg agt gaa    576
Ser Leu Ser Leu Arg Arg Glu Ile Ser Leu Gln Glu Ala Met Ser Glu
        180                 185                 190 atc gcc gag tgg caa ctc cag cca tta ccc att agt ggc tta tgt tac    624
Ile Ala Glu Trp Gln Leu Gln Pro Leu Pro Ile Ser Gly Leu Cys Tyr
    195                 200                 205 ttc gac aat gcg ttg tgg atc cgc ctt gag ggc ggc gaa gga tcg gta    672
Phe Asp Asn Ala Leu Trp Ile Arg Leu Glu Gly Gly Glu Gly Ser Val
210                 215                 220 aaa gca gcg cgt gaa ctg ctg ggt ggc gaa gag gtt gcc ggt cag ttc    720
Lys Ala Ala Arg Glu Leu Leu Gly Gly Glu Glu Val Ala Gly Gln Phe
225                 230                 235                 240 tgg cag caa ttg cgt gaa caa caa ctg ccg ttc ttc tcg tta cca ggt    768
Trp Gln Gln Leu Arg Glu Gln Gln Leu Pro Phe Phe Ser Leu Pro Gly
            245                 250                 255 acc tta tgg cgc att tca tta ccc agt gat gcg ccg atg atg gat tta    816
Thr Leu Trp Arg Ile Ser Leu Pro Ser Asp Ala Pro Met Met Asp Leu
        260                 265                 270 ccc ggc gag caa ctg atc gac tgg ggc ggg gcg tta cgc tgg ctg aaa    864
Pro Gly Glu Gln Leu Ile Asp Trp Gly Gly Ala Leu Arg Trp Leu Lys
    275                 280                 285 tcg aca gcc gag gac aat caa atc cat cgc atc gcc cgc aac gct ggc    912
Ser Thr Ala Glu Asp Asn Gln Ile His Arg Ile Ala Arg Asn Ala Gly
290                 295                 300 ggt cat gcg acc cgc ttt agt gcc gga gat ggt ggc ttt gcc ccg cta    960
Gly His Ala Thr Arg Phe Ser Ala Gly Asp Gly Gly Phe Ala Pro Leu
305                 310                 315                 320 tcg gct cct tta ttc cgc tat cac cag cag ctt aaa cag cag ctc gac   1008
Ser Ala Pro Leu Phe Arg Tyr His Gln Gln Leu Lys Gln Gln Leu Asp
            325                 330                 335 cct tgc ggc gtg ttt aac ccc ggt cgc atg tac gcg gaa ctt tga       1053
Pro Cys Gly Val Phe Asn Pro Gly Arg Met Tyr Ala Glu Leu
        340                 345                 350

<210> SEQ ID NO 4
<211> LENGTH: 350
<212> TYPE: PRT
<213> ORGANISM: Escherichia coli

<400> SEQUENCE: 4

Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60
```

```
Ala Arg Val Gly Thr Pro Leu Val Thr Ile Glu Ala Ala Leu Glu Ser
 65                  70                  75                  80

Ala Gly Gln Met Leu Pro Cys Glu Pro Pro His Tyr Gly Glu Glu Ala
                 85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
130                 135                 140

Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
210                 215                 220

Lys Ala Ala Arg Glu Leu Leu Gly Gly Glu Val Ala Gly Gln Phe
225                 230                 235                 240

Trp Gln Gln Leu Arg Glu Gln Leu Pro Phe Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285

Ser Thr Ala Glu Asp Asn Gln Ile His Arg Ile Ala Arg Asn Ala Gly
290                 295                 300

Gly His Ala Thr Arg Phe Ser Ala Gly Asp Gly Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
            340                 345                 350

<210> SEQ ID NO 5
<211> LENGTH: 1224
<212> TYPE: DNA
<213> ORGANISM: Escherichia coli
<220> FEATURE:
<221> NAME/KEY: CDS
<222> LOCATION: (1)..(1221)
<223> OTHER INFORMATION: gcl F

<400> SEQUENCE: 5 atg caa acc caa tta act gaa gag atg cgg cag aac gcg cgc gcg ctg     48
Met Gln Thr Gln Leu Thr Glu Glu Met Arg Gln Asn Ala Arg Ala Leu
 1               5                  10                  15 gaa gcc gac agc atc ctg cgc gcc tgt gtt cac tgc gga ttt tgt acc     96
Glu Ala Asp Ser Ile Leu Arg Ala Cys Val His Cys Gly Phe Cys Thr
             20                  25                  30 gca acc tgc cca acc tat cag ctt ctg ggc gat gaa ctg gac ggg ccg    144
Ala Thr Cys Pro Thr Tyr Gln Leu Leu Gly Asp Glu Leu Asp Gly Pro
         35                  40                  45 cgc ggg cgc atc tat ctg att aaa cag gtg ctg gaa ggc aac gaa gtc    192
```

```
                Arg Gly Arg Ile Tyr Leu Ile Lys Gln Val Leu Glu Gly Asn Glu Val
                    50                  55                  60 acg ctt aaa aca cag gag cat ctc gat cgc tgc ctc act tgc cgt aat          240
Thr Leu Lys Thr Gln Glu His Leu Asp Arg Cys Leu Thr Cys Arg Asn
 65                  70                  75                  80 tgt gaa acc acc tgt cct tct ggt gtg cgc tat cac aat ttg ctg gat          288
Cys Glu Thr Thr Cys Pro Ser Gly Val Arg Tyr His Asn Leu Leu Asp
                     85                  90                  95 atc ggg cgt gat att gtc gag cag aaa gtg aaa cgc cca ctg ccg gag          336
Ile Gly Arg Asp Ile Val Glu Gln Lys Val Lys Arg Pro Leu Pro Glu
                100                 105                 110 cga ata ctg cgc gaa gga ttg cgc cag gta gtg ccg cgt ccg gcg gtc          384
Arg Ile Leu Arg Glu Gly Leu Arg Gln Val Val Pro Arg Pro Ala Val
                115                 120                 125 ttc cgt gcg ctg acg cag gta ggg ctg gtg ctg cga ccg ttt tta ccg          432
Phe Arg Ala Leu Thr Gln Val Gly Leu Val Leu Arg Pro Phe Leu Pro
130                 135                 140 gaa cag gtc aga gca aaa ctg cct gct gaa acg gtg aaa gct aaa ccg          480
Glu Gln Val Arg Ala Lys Leu Pro Ala Glu Thr Val Lys Ala Lys Pro
145                 150                 155                 160 cgt ccg ccg ctg cgc cat aag cgt cgg gtt tta atg ttg gaa ggc tgc          528
Arg Pro Pro Leu Arg His Lys Arg Arg Val Leu Met Leu Glu Gly Cys
                165                 170                 175 gcc cag cct acg ctt tcg ccc aac acc aac gcg gca act gcg cga gtg          576
Ala Gln Pro Thr Leu Ser Pro Asn Thr Asn Ala Ala Thr Ala Arg Val
                180                 185                 190 ctg gat cgt ctg ggg atc agc gtc atg cca gct aac gaa gca ggc tgt          624
Leu Asp Arg Leu Gly Ile Ser Val Met Pro Ala Asn Glu Ala Gly Cys
                195                 200                 205 tgt ggc gcg gtg gac tat cat ctt aat gcg cag gag aaa ggg ctg gca          672
Cys Gly Ala Val Asp Tyr His Leu Asn Ala Gln Glu Lys Gly Leu Ala
210                 215                 220 cgg gcg cgc aat aat att gat gcc tgg tgg ccc gcg att gaa gca ggt          720
Arg Ala Arg Asn Asn Ile Asp Ala Trp Trp Pro Ala Ile Glu Ala Gly
225                 230                 235                 240 gcc gag gca att ttg caa acc gcc agc ggc tgc ggc gcg ttt gtc aaa          768
Ala Glu Ala Ile Leu Gln Thr Ala Ser Gly Cys Gly Ala Phe Val Lys
                245                 250                 255 gag tat ggg cag atg ctg aaa aac gat gcg tta tat gcc gat aaa gca          816
Glu Tyr Gly Gln Met Leu Lys Asn Asp Ala Leu Tyr Ala Asp Lys Ala
                260                 265                 270 cgt cag gtc agt gaa ctg gcg gtc gat tta gtc gaa ctt ctg cgc gag          864
Arg Gln Val Ser Glu Leu Ala Val Asp Leu Val Glu Leu Leu Arg Glu
                275                 280                 285 gaa ccg ctg gaa aaa ctg gca att cgc ggc gat aaa aag ctg gcc ttc          912
Glu Pro Leu Glu Lys Leu Ala Ile Arg Gly Asp Lys Lys Leu Ala Phe
290                 295                 300 cac tgt ccg tgt acc cta caa cat gcg caa aag ctg aac ggc gaa gtg          960
His Cys Pro Cys Thr Leu Gln His Ala Gln Lys Leu Asn Gly Glu Val
305                 310                 315                 320 gaa aaa gtg ttg ctt cgt ctt gga ttt acc tta acg gac gtt ccc gac         1008
Glu Lys Val Leu Leu Arg Leu Gly Phe Thr Leu Thr Asp Val Pro Asp
                325                 330                 335 agc cat ctg tgc tgc ggt tca gcg gga aca tat gcg tta acg cat ccc         1056
Ser His Leu Cys Cys Gly Ser Ala Gly Thr Tyr Ala Leu Thr His Pro
                340                 345                 350 gat ctg gca cgc cag ctg cgg gat aac aaa atg aat gcg ctg gaa agc         1104
Asp Leu Ala Arg Gln Leu Arg Asp Asn Lys Met Asn Ala Leu Glu Ser
                355                 360                 365
```

```
                                           -continued ggc aaa ccg gaa atg atc gtc acc gcc aac att ggt tgc cag acg cat    1152
Gly Lys Pro Glu Met Ile Val Thr Ala Asn Ile Gly Cys Gln Thr His
    370             375                 380 ctg gcg agc gcc ggt cgt acc tct gtg cgt cac tgg att gaa att gta    1200
Leu Ala Ser Ala Gly Arg Thr Ser Val Arg His Trp Ile Glu Ile Val
385                 390                 395                 400 gaa caa gcc ctt gaa aag gaa taa                                    1224
Glu Gln Ala Leu Glu Lys Glu
                405

<210> SEQ ID NO 6
<211> LENGTH: 407
<212> TYPE: PRT
<213> ORGANISM: Escherichia coli

<400> SEQUENCE: 6

Met Gln Thr Gln Leu Thr Glu Glu Met Arg Gln Asn Ala Arg Ala Leu
1               5                   10                  15

Glu Ala Asp Ser Ile Leu Arg Ala Cys Val His Cys Gly Phe Cys Thr
                20                  25                  30

Ala Thr Cys Pro Thr Tyr Gln Leu Leu Gly Asp Glu Leu Asp Gly Pro
            35                  40                  45

Arg Gly Arg Ile Tyr Leu Ile Lys Gln Val Leu Glu Gly Asn Glu Val
        50                  55                  60

Thr Leu Lys Thr Gln Glu His Leu Asp Arg Cys Leu Thr Cys Arg Asn
65                  70                  75                  80

Cys Glu Thr Thr Cys Pro Ser Gly Val Arg Tyr His Asn Leu Leu Asp
                85                  90                  95

Ile Gly Arg Asp Ile Val Glu Gln Lys Val Lys Arg Pro Leu Pro Glu
            100                 105                 110

Arg Ile Leu Arg Glu Gly Leu Arg Gln Val Val Pro Arg Pro Ala Val
        115                 120                 125

Phe Arg Ala Leu Thr Gln Val Gly Leu Val Leu Arg Pro Phe Leu Pro
    130                 135                 140

Glu Gln Val Arg Ala Lys Leu Pro Ala Glu Thr Val Lys Ala Lys Pro
145                 150                 155                 160

Arg Pro Pro Leu Arg His Lys Arg Arg Val Leu Met Leu Glu Gly Cys
                165                 170                 175

Ala Gln Pro Thr Leu Ser Pro Asn Thr Asn Ala Ala Thr Ala Arg Val
            180                 185                 190

Leu Asp Arg Leu Gly Ile Ser Val Met Pro Ala Asn Glu Ala Gly Cys
        195                 200                 205

Cys Gly Ala Val Asp Tyr His Leu Asn Ala Gln Glu Lys Gly Leu Ala
    210                 215                 220

Arg Ala Arg Asn Asn Ile Asp Ala Trp Trp Pro Ala Ile Glu Ala Gly
225                 230                 235                 240

Ala Glu Ala Ile Leu Gln Thr Ala Ser Gly Cys Gly Ala Phe Val Lys
                245                 250                 255

Glu Tyr Gly Gln Met Leu Lys Asn Asp Ala Leu Tyr Ala Asp Lys Ala
            260                 265                 270

Arg Gln Val Ser Glu Leu Ala Val Asp Leu Val Glu Leu Leu Arg Glu
        275                 280                 285

Glu Pro Leu Glu Lys Leu Ala Ile Arg Gly Asp Lys Lys Leu Ala Phe
    290                 295                 300

His Cys Pro Cys Thr Leu Gln His Ala Gln Lys Leu Asn Gly Glu Val
305                 310                 315                 320
```

```
Glu Lys Val Leu Leu Arg Leu Gly Phe Thr Leu Thr Asp Val Pro Asp
                325             330             335

Ser His Leu Cys Cys Gly Ser Ala Gly Thr Tyr Ala Leu Thr His Pro
            340             345             350

Asp Leu Ala Arg Gln Leu Arg Asp Asn Lys Met Asn Ala Leu Glu Ser
        355             360             365

Gly Lys Pro Glu Met Ile Val Thr Ala Asn Ile Gly Cys Gln Thr His
    370             375             380

Leu Ala Ser Ala Gly Arg Thr Ser Val Arg His Trp Ile Glu Ile Val
385             390             395             400

Glu Gln Ala Leu Glu Lys Glu
            405
```

METHOD FOR INCREASING PHOTOSYNTHETIC CARBON FIXATION USING GLYCOLATE DEHYDROGENASE MULTI-SUBUNIT FUSION PROTEIN

RELATED APPLICATIONS

This application is a national stage application (under 35 U.S.C. §371) of PCT/EP2011/051505, filed Feb. 3, 2011, which claims priority of European application 10152714.1 filed on Feb. 4, 2010, and U.S. Provisional application 61/368,012, filed Jul. 27, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 5500_181_US_SEQ_LIST. The size of the text file is 30 KB, and the text file was created on Aug. 2, 2012.

Crop productivity is influenced by many factors, among which are, on the one hand factors influencing the capacity of the plant to produce biomass (photosynthesis, nutrient and water uptake), and on the other hand factors influencing the capacity of the plant to resist certain stresses, like biotic stresses (insects, fungi, viruses . . . ) or abiotic stresses (drought, salinity, nutrient starvation . . . ).

One important factor influencing the production of biomass is photosynthesis. Photosynthesis is the mechanism through which plants capture atmospheric carbon dioxide and transform it into sugar, which is then incorporated into plant tissues, thereby creating biomass. Photosynthesis is the ultimate source of all primary productivity on earth.

Most plants have a photosynthetic mechanism in which the chloroplastic enzyme RuBisCo (Ribulose-1,5-Bisphosphate Carboxylase/Oxygenase) is the main enzyme capturing carbon dioxide and transforming it into sugar. Those plants, including some of the most important crop plants, e.g. rice, wheat, barley, potato, rapeseed, belong to the so-called $C_3$ plants. One known problem in the photosynthetic mechanism of C3 plants is that the efficiency of carbon fixation is not optimal in certain environmental conditions where part of the fixed carbon is lost through the alternative activity of RuBisCo called oxygenation.

RuBisCO is able to catalyze both the carboxylation and oxygenation of ribulose-1,5-bisphosphate. The balance between these two activities depends mainly on the $CO_2/O_2$ ratio in the leaves, which may change following the plant's reaction to certain environmental conditions. Each carboxylation reaction produces two molecules of phosphoglycerate that enter the Calvin cycle, ultimately to form starch and sucrose and to regenerate ribulose-1,5-bisphosphate. The oxygenation reaction produces single molecules of phosphoglycerate and phosphoglycolate. The latter is recycled into phosphoglycerate by photorespiration (Leegood R. C. et al, 1995). One molecule of $CO_2$ is released for every two molecules of phosphoglycolate produced, resulting in a net loss of fixed carbon that ultimately reduces the production of sugars and biomass. Ammonia is also lost in this reaction, and needs to be refixed through energy consuming reactions in the chloroplast.

Overcoming photorespiration has been reported as a target for raising the maximum efficiency of photosynthesis and enhancing its productivity (Zhu et al., 2008) and several attempts have been described so far to reduce the loss of carbon in plants and therefore to increase the production of sugars and biomass.

Kebeish et al. reported that the photorespiratory losses in *Arabidopsis thaliana* can be alleviated by introducing into chloroplasts a bacterial pathway for the catabolism of the photorespiratory intermediate, glycolate (WO 03/100066; Kebeish R. et al., 2007). The authors first targeted the three subunits of *Escherichia coli* glycolate dehydrogenase to *Arabidopsis thaliana* chloroplasts and then introduced the *Escherichia coli* glyoxylate carboligase and *Escherichia coli* tartronic semialdehyde reductase to complete the pathway that converts glycolate to glycerate in parallel with the endogenous photorespiratory pathway. This step-wise nuclear transformation with the five *Escherichia coli* genes leads to *Arabidopsis* plants in which chloroplastic glycolate is converted directly to glycerate. These transgenic plants grew faster, produced more shoot and root biomass, and contained more soluble sugars.

In PCT/EP2009/059843, a method for increasing biomass production and/or seed production and/or carbon fixation in rice plants is disclosed, wherein the rice plant is transformed with the three subunits (glcD, glcE and glcF) of *Escherichia coli* glycolate dehydrogenase, without subsequent introduction of the *Escherichia coli* glyoxylate carboligase and *Escherichia coli* tartronic semialdehyde reductase.

The objective of the present invention is to exploit translational fusions of the subunits bacterial multi-subunit glycolate dehydrogenase (GDH) enzymes in crops avoiding the time-consuming and cumbersome process of multiple transformations or of transformation with multiple expression cassettes. The bacterial glcD, glcE and glcF subunits have been fused with flexible linkers in different arrangements and tested in *E. coli* strains deficient in GDH demonstrating that the recombinant GDH multi-subunit fusion proteins DEFp, EFDp and FDEp are active. Best performing constructs have been transferred to *Nicotiana tabacum*, rice and rapeseed plants and transgenic plants showed significant increased growth and improved photosynthetic rate.

The present invention relates to a method for increasing biomass production and/or seed production and/or carbon fixation in plants comprising introducing into the genome of a plant cell a nucleic acid encoding a glycolate dehydrogenase multi-subunit fusion protein, wherein said introduction of said one nucleic acid results in a de novo expression of one synthetic polypeptide having the enzymatic activity of a glycolate dehydrogenase and wherein said one polypeptide is localized in chloroplasts of the plant produced.

In the context of the invention, a glycolate dehydrogenase multi-subunit fusion protein is one polypeptide consisting of the subunits of a glycolate dehydrogenase that are essential for glycolate dehydrogenase activity, generally with peptide linkers in between these subunits.

In the present invention we selected the repetitive linker sequence $(Gly_4Ser)_3$ suited to connect covalently the bacterial glcD, glcE and glcF domains into a polyprotein format without interfering with the desired properties such as proper folding, solubility and GDH activity. Furthermore, the linker should not be subjected to the proteases cleavage in the plant cytosol, allowing the polyprotein overexpression in chloroplasts.

In the context of the invention, biomass is the quantity of matter produced by individual plants, or by surface area on which the plants are grown. Several parameters may be measured in order to determine the increase of biomass production. Examples of such parameters are the height of the plant, surface of the leave blade, shoot dry weight, root dry weight, seed number, seed weight, seed size . . . . Seed production or seed yield can be measured per individual plant or per surface area where the plants are grown.

These parameters are generally measured after a determined period of growth in soil or at a specific step of growth, for example at the end of the vegetative period, and compared between plants transformed with the one or more nucleic acids according to the invention and plants not transformed with such one or more nucleic acids.

The increase of carbon fixation by the plant can be determined by measuring gas exchange and chlorophyll fluorescence parameters. A convenient methodology, using the LI-6400 system (Li-Cor) and the software supplied by the manufacturer, is described in R. Kebeish et al., 2007, and is incorporated herein by reference.

The nucleic acid involved in the method of the invention encodes one polypeptide having the enzymatic activity of a glycolate dehydrogenase.

The glycolate dehydrogenase activity can be assayed according to Lord J. M. 1972, using the technology described in example 6 of the present application.

Alternatively, complementation analysis with mutants of E. coli deficient in the three subunits forming active endogenous glycolate dehydrogenase may be performed. These mutants of E. coli are incapable of growing on glycolate as the sole carbon source. When the overexpression of an enzyme in these deficient mutants restores the growth of the bacteria on the medium containing glycolate as the sole carbon source, it means that this enzyme encodes a functional equivalent to the E. coli glycolate dehydrogenase. The method and means for the complementation analysis is described in Bari et al, 2004, and incorporated herein by reference.

Nucleic acid molecules encoding one polypeptide having the enzymatic activity of a glycolate dehydrogenase may be produced by means of recombinant DNA techniques (e.g. PCR), or by means of chemical synthesis. The identification and isolation of such nucleic acid molecules may take place by using the sequences, or part of those sequences, of the known glycolate dehydrogenases nucleic acid molecules or, as the case may be, the reverse complement strands of these molecules, e.g. by hybridization according to standard methods (see e.g. Sambrook et al., 1989).

The glycolate dehydrogenase for the purpose of the invention can be any naturally-occurring glycolate dehydrogenase, or any active fragment thereof or any variant thereof wherein some amino acids (preferably 1 to 20 amino acids, more preferably 1 to 10, even more preferably 1 to 5) have been replaced, added or deleted such that the enzyme retains its glycolate dehydrogenase activity.

According to the present invention, a "nucleic acid" or "nucleic acid molecule" is understood as being a polynucleotide molecule which can be of the DNA or RNA type, preferably of the DNA type, and in particular double-stranded. It can be of natural or synthetic origin. Synthetic nucleic acids are generated in vitro. Examples of such synthetic nucleic acids are those in which the codons which encode polypeptide(s) having the enzymatic activity of a glycolate dehydrogenase according to the invention have been optimized in accordance with the host organism in which it is to be expressed (e.g., by replacing codons with those codons more preferred or most preferred in codon usage tables of such host organism or the group to which such host organism belongs, compared to the original host). Methods for codon optimization are well known to the skilled person.

Preferred glycolate dehydrogenase multi-subunit fusion proteins are those consisting of the fusion of bacterial glycolate dehydrogenase subunits, more preferably those consisting of the fusion of the three essential subunits encoded by the E. coli glc operon (gi/1141710/gb/L43490.1/ECOGLCC). Most preferred are polypeptides which comprise the fused amino acid sequences of SEQ ID NOs: 2 (Glc D), 4 (Glc E) and 6 (Glc F), wherein these amino sequences may be linked by a linker. Accordingly, a nucleic acid comprising the polynucleotide sequences of SEQ ID NOs: 1, 3 and 5 can be used for performing the present invention.

The method of the invention encompasses the introduction into the genome of a plant cell of a nucleic acid encoding a glycolate dehydrogenase multi-subunit fusion protein, having the enzymatic activity of a glycolate dehydrogenase, wherein said polypeptide comprises sequences having a sequence identity of at least 60, 70, 80 or 90%, particularly at least 95%, 97%, 98% or at least 99% at the amino acid sequence level with SEQ ID NO: 2, 4, and 6 respectively, wherein the introduction of the nucleic acid(s) result in a de novo expression of one polypeptide having the enzymatic activity of a glycolate dehydrogenase, and wherein said activity is located inside the chloroplasts.

The method of the invention encompasses also the introduction into the genome of a plant cell of a nucleic acid encoding a glycolate dehydrogenase multi-subunit fusion protein, having the enzymatic activity of a glycolate dehydrogenase, wherein said nucleic acid comprises nucleic acid sequences with at least 60, 70, 80 or 90%, particularly at least 95%, 97%, 98% or at least 99%, sequence identity to the nucleotide sequences of SEQ ID NO: 1, 3, and 5 respectively, wherein the introduction of the nucleic acid results in a de novo expression of at least one polypeptide having the enzymatic activity of a glycolate dehydrogenase, and wherein said activity is located inside the chloroplasts.

For the purpose of this invention, the "sequence identity" of two related nucleotide or amino acid sequences, expressed as a percentage, refers to the number of positions in the two optimally aligned sequences which have identical residues ($\times 100$) divided by the number of positions compared. A gap, i.e a position in an alignment where a residue is present in one sequence but not in the other, is regarded as a position with non-identical residues. The alignment of the two sequences can be performed by the Needleman and Wunsch algorithm (Needleman and Wunsch 1970) in EMBOSS (Rice et al., 2000) to find optimum alignment over the entire length of the sequences, using default settings (gap opening penalty 10, gap extension penalty 0.5).

Once the sequence of a foreign DNA is known, primers and probes can be developed which specifically recognize these sequences in the nucleic acid (DNA or RNA) of a sample by way of a molecular biological technique. For instance, a PCR method can be developed to identify the genes used in the method of the invention (gdh genes) in biological samples (such as samples of plants, plant material or products comprising plant material). Such a PCR is based on at least two specific "primers", e.g., both recognizing a sequence within the gdh coding region used in the invention (such as the coding region of SEQ ID No. 1, 3, 5), or one recognizing a sequence within the gdh coding region and the other recognizing a sequence within the associated transit peptide sequence or within the regulatory regions such as the promoter or 3' end of the chimeric gene comprising a gdh DNA used in the invention. The primers preferably have a sequence of between 15 and 35 nucleotides which under optimized PCR conditions specifically recognize a sequence within the gdh chimeric gene used in the invention, so that a specific fragment ("integration fragment" or discriminating amplicon) is amplified from a nucleic acid sample comprising a gdh gene used in the invention. This means that only the targeted integration fragment, and no other sequence in the plant genome or foreign DNA, is amplified under optimized PCR conditions.

The method of the invention encompasses also the introduction into the genome of a plant cell of a nucleic acid encoding a glycolate dehydrogenase multi-subunit fusion protein, having the enzymatic activity of a glycolate dehydrogenase, wherein said one nucleic acid hybridizes under stringent conditions to a nucleotide sequence selected from the group of SEQ ID NO 1, 3, and 5, wherein the introduction of the nucleic acid(s) result in a de novo expression of one polypeptide having the enzymatic activity of a glycolate dehydrogenase, and wherein said activity is located inside the chloroplasts. Stringent hybridization conditions, as used herein, refers particularly to the following conditions: immobilizing the relevant DNA sequences on a filter, and prehybridizing the filters for either 1 to 2 hours in 50% formamide, 5% SSPE, 2×Denhardt's reagent and 0.1% SDS at 42° C., or 1 to 2 hours in 6×SSC, 2×Denhardt's reagent and 0.1% SDS at 68° C. The denatured dig- or radio-labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions.

The terminology DNA or protein "comprising" a certain sequence X, as used throughout the text, refers to a DNA or protein including or containing at least the sequence X, so that other nucleotide or amino acid sequences can be included at the 5' (or N-terminal) and/or 3' (or C-terminal) end, e.g. (the nucleotide sequence encoding) a selectable marker protein, (the nucleotide sequence encoding) a transit peptide, and/or a 5' leader sequence or a 3' trailer sequence. Similarly, use of the term "comprise", "comprising" or "comprises" throughout the text and the claims of this application should be understood to imply the inclusion of a stated integer or step or group of integers or steps but not the exclusion of any other integer or step or group of integers or steps The method of the present invention consists in installing a glycolate dehydrogenase activity inside the chloroplast. This can be done either by introducing the nucleic acid encoding the glycolate dehydrogenase activity into the nuclear genome of plant cells, the coding sequence of the protein then being fused to a nucleic acid encoding a chloroplast transit peptide. Alternatively, the glycolate dehydrogenase activity can be put into the chloroplast by direct transformation of the chloroplast genome with the nucleic acid(s) encoding the corresponding enzyme.

General techniques for transforming plant cells or plants tissues can be used. One series of methods comprises bombarding cells, protoplasts or tissues with particles to which the DNA sequences are attached. Another series of methods comprises using, as the means for transfer into the plant, a chimeric gene which is inserted into an *Agrobacterium tumefaciens* Ti plasmid or an *Agrobacterium rhizogenes* Ri plasmid. Other methods may be used, such as microinjection or electroporation or otherwise direct precipitation using PEG. The skilled person can select any appropriate method and means for transforming the plant cell or the plant.

For the purpose of expressing the nucleic acid which encodes the polypeptide having the enzymatic activity as required for the present invention in plant cells, any convenient regulatory sequences can be used. The regulatory sequences will provide transcriptional and translational initiation as well as termination regions, where the transcriptional initiation may be constitutive or inducible. The coding region is operably linked to such regulatory sequences. Suitable regulatory sequences are represented by the constitutive 35S promoter. Alternatively, the constitutive ubiquitin promoter can be used, in particular the maize ubiquitin promoter (GenBank: gi19700915). Examples for inducible promoters represent the light inducible promoters of the small subunit of RUBISCO and the promoters of the "light harvesting complex binding proteins (lhcb)". Advantageously, the promoter region of the gos2 gene of *Oryza sativa* including the 5' UTR of the GOS2 gene with intron (de Pater et al., 1992), the promoter region of the ribulose-1,5-biphosphate carboxylase small subunit gene of *Oryza sativa* (Kyozuka J. et al., 1993), or the promoter region of the actin 1 gene of *Oryza sativa* (McElroy D. et al., 1990) may be used.

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, for example, or introns such as the adh1 intron of maize or intron 1 of rice actin.

As a regulatory terminator or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in Application EP 0 633 317.

In one particular embodiment of the invention whereby transformation of the nuclear genome is preferred, a nucleic acid which encodes a chloroplast transit peptide is employed 5' of the nucleic acid sequence encoding a glycolate dehydrogenase, with this transit peptide sequence being arranged between the promoter region and the nucleic acid encoding the glycolate dehydrogenase so as to permit expression of a transit peptide/glycolate dehydrogenase fusion protein. The transit peptide makes it possible to direct the glycolate dehydrogenase into the plastids, more especially the chloroplasts, with the fusion protein being cleaved between the transit peptide and the glycolate dehydrogenase when the latter enters the plastid. The transit peptide may be a single peptide, such as an EPSPS transit peptide (described in U.S. Pat. No. 5,188,642) or a transit peptide of the plant ribulose biscarboxylase/oxygenase small subunit (RuBisCO ssu), for example the chloroplast transit peptide derived from the ribulose-1,5-bisphosphate carboxylase gene from *Solanum tuberosum* (GenBank: gene gi21562, encoding the protein G68077, amino acids 1-58), where appropriate including a few amino acids of the N-terminal part of the mature RuBisCO ssu (EP 189 707), or the chloroplast targeting peptide of the potato rbcS1 gene (gi21562). A transit peptide may be the whole naturally occurring (wild-type) transit peptide, a functional fragment thereof, a functional mutant thereof. It can also be a chimeric transit peptide wherein at least two transit peptides are associated to each other or wherein parts of different transit peptides are associated to each other in a functional manner. One example of such chimeric transit peptide comprises a transit peptide of the sunflower RuBisCO ssu fused to the N-terminal part of the maize RuBisCO ssu, fused to the transit peptide of the maize RuBisCO ssu, as described in patent EP 508 909.

Alternatively, the polypeptides may be directly expressed into the chloroplast using transformation of the chloroplast genome. Methods for integrating nucleic acids of interest into the chloroplast genome are known in the art, in particular methods based on the mechanism of homologous recombination. Suitable vectors and selection systems are known to the person skilled in the art. The coding sequences for the polypeptides may either be transferred in individual vectors or in one construct, where the individual open reading frames may be fused to one or several polycistronic RNAs with ribosome binding sites added in front of each individual open reading frame in order to allow independent translation. An example of means and methods which can be used for such integration into the chloroplast genome is given for example in WO 06/108830, the content of which are hereby incorporated by reference.

When the nucleic acids are directly integrated into the chloroplast genome, a transit peptide sequence is not required. In that case, the (Met) translation start codon may be added to the sequence encoding a mature protein to ensure initiation of translation.

Subject-matter of the present invention also are nucleic acids encoding a glycolate dehydrogenase multi-subunit fusion protein.

In a particular embodiment, the nucleic acid of the invention encodes a glycolate dehydrogenase multi-subunit fusion protein which comprises an amino acid sequence which targets said protein to the chloroplast.

In another particular embodiment, the nucleic acid of the invention encodes a glycolate dehydrogenase multi-subunit fusion protein which is the fusion of bacterial glycolate dehydrogenase subunits.

In another particular embodiment, the nucleic acid of the invention encodes a glycolate dehydrogenase multi-subunit fusion protein which is the fusion of the three subunits encoded by the *E. coli* glc operon.

In another particular embodiment, the nucleic acid of the invention encodes a glycolate dehydrogenase multi-subunit fusion protein which comprises amino acids sequences having at least 60% sequence identity to the sequences of SEQ ID NOs 2, 4 and 6 respectively.

In another particular embodiment, the nucleic acid of the invention encodes a glycolate dehydrogenase multi-subunit fusion protein which comprises polynucleotides sequences having at least 60% sequence identity to the polynucleotides sequences of SEQ ID NOs 1, 3 and 5 respectively.

Subject-matter of the present invention also are plant cells, plant tissues, plants and part or seed thereof, comprising one nucleic acid encoding a glycolate dehydrogenase multi-subunit fusion protein and expressing inside the chloroplast one polypeptide having the enzymatic activity of glycolate dehydrogenase.

Particular embodiments of the nucleic acids introduced into the plant cells, plant tissues, plants and part or seed thereof are mentioned above.

The present invention also relates to plants which contain transformed cells, in particular plants which are regenerated from the transformed cells. The regeneration can be obtained by any appropriate method. The following patents and patent applications may be cited, in particular, with regard to the methods for transforming plant cells and regenerating plants: U.S. Pat. No. 4,459,355, U.S. Pat. No. 4,536,475, U.S. Pat. No. 5,464,763, U.S. Pat. No. 5,177,010, U.S. Pat. No. 5,187,073, EP 267,159, EP 604 662, EP 672 752, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat. No. 5,565,346, U.S. Pat. No. 5,484,956, U.S. Pat. No. 5,508,468, U.S. Pat. No. 5,538,877, U.S. Pat. No. 5,554,798, U.S. Pat. No. 5,489,520, U.S. Pat. No. 5,510,318, U.S. Pat. No. 5,204,253, U.S. Pat. No. 5,405,765, EP 442 174, EP 486 233, EP 486 234, EP 539 563, EP 674 725, WO 91/02071 and WO 95/06128.

The present invention also relates to transformed plants or part thereof, which are derived by cultivating and/or crossing the above regenerated plants, and to the seeds of the transformed plants, characterized in that they contain a transformed plant cell according to the invention.

In a particular embodiment of the invention, the transformed plants, or part thereof, are selected among rice, wheat, barley, potato, rapeseed, tobacco.

In a particular embodiment of the invention, the transgenic seeds, and meal, oil or food obtained thereof, are from rice, wheat, barley, rapeseed, or tobacco plants.

The present invention also relates to any products such as the meal which are obtained by processing the plants, part thereof, or seeds of the invention. For example, the invention encompasses grains obtained from the processing of the seeds according to the invention, but also meal obtained from the further processing of the seeds or the grains, as well as any food product obtained from said meal.

Sequence Listing:
SEQ ID NO 1: *Escherichia coli* gcl D DNA sequence
SEQ ID NO 2: amino acid sequence encoded by SEQ ID NO 1
SEQ ID NO 3: *Escherichia coli* gcl E DNA sequence
SEQ ID NO 4: amino acid sequence encoded by SEQ ID NO 3
SEQ ID NO 5: *Escherichia coli* gcl F DNA sequence
SEQ ID NO 6: amino acid sequence encoded by SEQ ID NO 5

FIGURES

FIG. 1: Design of the synthetic multi-subunit fusion cassettes. glcD, glcE and glcF: bacterial genes encoding for the subunits D, E and F of the GDH. I: $(Gly_4Ser)_3$ linker. T: His6 tag. Arrow: enterokinase cleavage site. The introduced restriction sites are indicated.

Figure 2:
Figure 2:
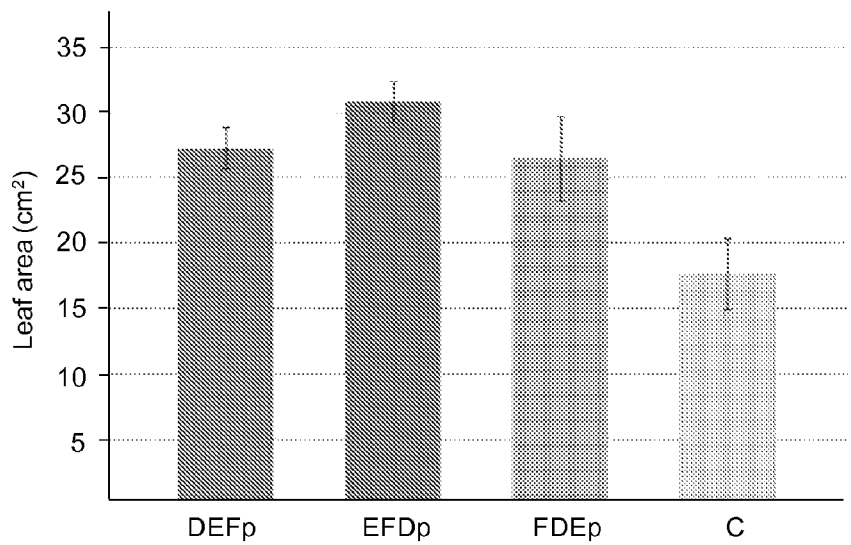

FIG. 2: Growth parameters of transgenic and non-transgenic lines. A: Phenotype of 4 weeks old transgenic $T_0$ plants producing DEFp in chloroplast. B: Leaf area of 7 weeks old tobacco plants. DEFp (n=6), EFDp (n=5), FDEp (n=4), C: non-transgenic *N. tabacum* cv. Petit Havana SR1 plants (n=6)

EXAMPLE 1

Design of Synthetic Multi-Subunit Gene Constructs

The bacterial glcD, glcE and glcF cDNAs encoding for the subunits D, E and F of the GDH were fused with a flexible linker encoding for the $(Gly_4Ser)_3$ motif to a multi-subunit gene construct (FIG. 1).

Restriction sites indicated in FIG. 1 were introduced to allow rearrangement of the glcD, glcE and glcF subunits and subcloning of the multi-subunit cassettes into the bacterial and plant expression vectors. Furthermore, the internal restriction sites (PstI/SalI and NcoI/XhoI) were introduced to facilitate exchange of the $(Gly_4Ser)_3$ linker with other flexible linkers. In addition, the generation of two gene-fusions cassettes will be possible by deleting the cDNA in the middle position via the SalI/XhoI restriction sites.

The C-terminal His6 tag was introduced to enable the detection and purification of the recombinant proteins. To avoid a potential interference of the His6 tag on the enzymatic activity of the multi-subunit GDH enzyme an enterokinase cleavage site is added upstream of the His6 tag allowing the removal of the C-terminal tag.

EXAMPLE 2

Synthesis of the Multi-subunit Fusion Cassettes

Three multi-subunit fusion cassettes containing the three bacterial subunit cDNAs in three different arrangements glcD-glcE-glcF, glcE-glcF-glcD and glcF-glcD-glcE were designed and synthetic genes encoding for the corresponding polypeptides DEFp, EFDp and FDEp, respectively, were synthesized. Prior to synthesis, the synthetic genes were codon-optimized for maximum expression yields according to the *Brassica napus* codon usage. Furthermore, based on a genetic algorithm, the synthetic genes were simultaneously optimized for a large set of competing parameters, such as mRNA secondary structure, cryptic splice sites, codon and motif repeats, and homogenous GC content.

EXAMPLE 3

Complementation Analysis with Mutants of *E. coli* Deficient in the Three Subunits Forming Active Endogenous Glycolate Dehydrogenase To determine whether DEFp, EFDp and FDEp are capable of complementing glycolate oxidase mutants of *E. coli*, complementation analysis were done with the *E. coli* mutant JA155 which carry transposon insertion in the glcD subunit of the glc operon and is incapable of growing on glycolate as the sole carbon source. Overexpression of DEFp, EFDp and FDEp in this mutant restored the growth of bacteria in medium containing glycolate as the sole carbon source, indicating that all three polyproteins are functional in vivo and can complement for the glcD subunit of the active EcGO enzyme.

EXAMPLE 4

Subcloning of DEFp, EFDp and FDEp cDNAs into the Plant Expression Vectors

To evaluate the in vivo effect of the bacterial multi-subunit DEFp, EFDp and FDEp polyprotein on GDH activity and biomass production in *N. tabacum* cv. Petit Havanna SR1 plants, the cDNAs encoding DEFp, EFDp and FDEp were inserted into a plant expression vector enabling recombinant protein targeting to the plant cell chloroplasts. Transgene expression is driven by the CaMV 35S promoter with duplicated enhancer region.

The synthesized DEFp cDNA was initially inserted into the pTRAkc shuttle vector using the EcoRI and XbaI restriction sites upstream of the CaMV 35S terminator generating the pTRA-nptII-DEFp plasmid. The pTRA plasmid contains the scaffold attachment region of the tobacco RB7 gene (gi3522871) and the nptII cassette of pPCV002 (Konz and Schell, 1986) for selection of transgenic plants on kanamycin (FIG. 2). Subsequently, the constitutive double enhanced CaMV 35S promoter, the 5' untranslated region of the chalcone synthase gene and the chloroplast targeting peptide sequence of the potato rbcS1 gene were amplified by PCR using as template the pTRAkc-rbcs1-cTP plasmid. The amplified PCR fragment was then subcloned into the pTRA-nptII-DEF using the AscI and AatII restriction sites.

The cloning of EFDp and FDEp cDNAs into the plant expression vector was performed in a similar way. The three final constructs were designated: pTRA-355-rbcs-cTP:DEFp, pTRA-35S-rbcs-cTP:EFDp and pTRA-35S-rbcs-cTP:FDEp, respectively.

EXAMPLE 5

Tobacco Plant Transformation and Regeneration

The plant expression vectors were introduced into *Agrobacterium tumefaciens* GV3101 cells using a Gene Pulser II electroporation system (BioRad, Hercules, Calif., USA) according to the manufacturer's instructions. To investigate the effect of the DEFp, EFDp and FDEp accumulation in the stably transformed tobacco plants (*N. tabacum* cv. Petit Havana SR1), transgenic $T_0$ plants were generated by leaf disk transformation with recombinant *A. tumefaciens* (Horsch et al., 1985) using kanamycin as a selection marker. The generated plants were cultivated in the glasshouse in DE73 standard soil with a 16 h natural daylight photoperiod and 22° C. daytime/20° C. night-time temperature.

Up to 33 transgenic $T_0$ plants were screened for the presence of the transgene and the recombinant protein by multiplex PCR and immunoblot analysis, respectively. 33-48% of the tested lines produced the DEFp, EFDp or FDEp, respectively, at the expected molecular size of 142 kDa. Seven $T_0$ lines showing the highest level of the recombinant proteins (0.03 to 0.09% of total soluble protein) were used to establish the $T_1$ generation.

EXAMPLE 6

Chloroplast Isolation and Enzymatic Assays

Intact chloroplasts are isolated using the procedure described by Kleffmann et al., 2007. These preparations are free of contaminating catalase and fumarase activity (>95% purity). Glycolate dehydrogenase activities are measured as described in Lord J. M., 1972. 100 µg of chloroplast protein extract is added to 100 µmol potassium phosphate (pH 8.0), 0.2 µmol DCIP, 0.1 ml 1% (w/v) PMS, and 10 µmol potassium glycolate in a final volume of 2.4 ml. At fixed time intervals, individual assays are terminated by the addition of 0.1 ml of 12 M HCl. After standing for 10 min, 0.5 ml of 0.1 M phenylhydrazine-HCl is added. The mixture is allowed to stand for a further 10 min, and then the extinction due to the formation of glyoxylate phenylhydrazone is measured at 324 nm.

EXAMPLE 7

$CO_2$ Release from Labeled Glycolate in Chloroplasts Extracts

1 µCi of [1,2-14C]-glycolate (Hartmann Analytics) is added to 50 µg of chloroplast protein extract in a tightly closed 15-ml reaction tube. Released $CO_2$ is absorbed in a 500-µl reaction tube containing 0.5 M NaOH attached to the inner wall of the 15-ml tube. Samples are incubated for 5 h and the gas phase in the reaction tube is frequently mixed with a syringe.

EXAMPLE 8

Assessment of Phenotype of Plants Expressing *E. coli* GDH

Growth of the transgenic plants producing the DEFp, EFDp or FDEp recombinant protein in the chloroplast, was monitored by the leaf area measurements according to the formula:

$$\text{leaf area (cm}^2\text{)} = 3.73 \cdot \left(\frac{\text{length} \cdot \text{width}}{100}\right) + 0.011 \cdot \left(\frac{\text{length} \cdot \text{width}}{100}\right)^2$$

Transgenic tobacco $T_0$ lines constitutively producing the DEFp, EFDp or FDEp, respectively, showed a significant increase of the leaf area (1.54-, 1.75- and 1.5-fold, respectively p<0.05), compared to non-transgenic control plants (FIG. 4). In addition, transgenic plants had more leaves than the wild type SR1 and additional small leaves besides the huge ones.

The photosynthetic performance of the transgenic plants was monitored via Licor LI-6400 by measurements of the apparent $CO_2$ assimilation and compensation point. The apparent rate of the $CO_2$ assimilation under ambient conditions was significantly enhanced in transgenic DEFp and EFDp plants compared to that of the wild type. Furthermore, the DEFp transgenic lines have a significant decrease (P<0.05) of $CO_2$ compensation points (54 p.p.m. $CO_2$) compared to control (64 p.p.m. $CO_2$), indicating higher photosynthetic rates for the DEFp $T_0$ lines.

Enhanced biomass and the reduced photorespiration was further confirmed in the $T_1$ (Table 1) and $T_2$ generation. Furthermore, the performance of the wild type and transgenic lines grown without fertilizer supplementation was analysed in the $T_1$ generation. Under these conditions, tobacco plants overexpressing the DEFp, EFDp and FDEp polyproteins showed reduced chlorosis and higher biomass production then the wild type control.

TABLE 1

Growth analysis of DEFp, EFDp or FDEp producing $T_1$, plants. All data are based on four independent biological replicates and standardized relative to azygous control plants (n > 15). Plants were grown without or with 2% fertilizer supplementation in water.

| | % increase FW +/− Fertilizer | % increase DW +/− Fertilizer | % increase height +/− Fertilizer | % decrease $CO_2$ c.P. | % decrease $O_2$ inhibition |
|---|---|---|---|---|---|
| DEFp | 8.2/27.5 | 19.3/17.3 | 32/54 | 9 | 5 |
| EFDp | 7.1/19 | 17.3/19.3 | 38/55 | 15 | 9 |
| FDEp | 14.9/31.7 | 22.3/22.5 | 31/52 | 13 | 10.5 |

Taken together, these data indicate that the plants producing the bacterial glycolate dehydrogenase polyprotein in their chloroplast have a significantly increased of biomass and improved photosynthetic rate.

The invention claimed is:

1. A method for increasing biomass production and/or seed production and/or carbon fixation in plants comprising introducing into the genome of a plant cell a nucleic acid encoding a glycolate dehydrogenase multi-subunit fusion protein, wherein said introduction of said one nucleic acid results in a de novo expression of one polypeptide having the enzymatic activity of a glycolate dehydrogenase and wherein said one polypeptide is localized in chloroplasts of the plant produced and wherein the glycolate dehydrogenase multi-subunit fusion protein comprises amino acid sequences having at least 95% sequence identify to the sequences of SEQ ID NO: 2, 4, and 6, respectively.

2. The method of claim 1, wherein said introduction of said one nucleic acid is done into the nuclear genome of the plant cells, and wherein said one nucleic acid encodes one polypeptide comprising an amino acid fragment that targets the polypeptide to the chloroplast.

3. The method of claim 1, wherein the nucleic acid encoding a glycolate dehydrogenase multi-subunit fusion protein comprises polynucleotides sequences having at least 95% sequence identity to the polynucleotides sequences of SEQ ID NOs 1, 3 and 5 respectively.

4. A nucleic acid encoding a glycolate dehydrogenase multi-subunit fusion protein, wherein said glycolate dehydrogenase multi-subunit fusion protein comprises amino acid sequences having at least 95% sequence to the sequences of SEQ ID NOs 2, 4, and 6, respectively.

5. A nucleic acid according to claim 4, wherein the glycolate dehydrogenase multi-subunit fusion protein comprises an amino acid sequence which targets said protein to the chloroplast.

6. A nucleic acid according to claim 4 wherein the nucleic acid encoding a glycolate dehydrogenase multi-subunit fusion protein comprises polynucleotides sequences having at least 95% sequence identity to the polynucleotides sequences of SEQ ID NOs 1, 3 and 5 respectively.

7. A transgenic plant cell comprising a nucleic acid encoding a glycolate dehydrogenase multi-subunit fusion protein of claim 4.

8. A transgenic plant cell according to claim 7, wherein the glycolate dehydrogenase multi-subunit fusion protein comprises an amino acid sequence which targets said protein to the chloroplast.

9. A transgenic plant, and part thereof, comprising a transgenic plant cell according to claim 7.

10. A transgenic plant, and part thereof, according to claim 9 selected among rice, wheat, barley, potato, rapeseed, tobacco.

11. A transgenic seed comprising a transgenic plant cell according to claim 7.

12. A transgenic seed according to claim 11 selected from the group consisting of rice, wheat, barley, rapeseed, and tobacco.

13. The method of claim 1, wherein said glycolate dehydrogenase multi-subunit fusion protein comprises the amino acid sequences of SEQ ID NO: 2, 4, and 6.

14. The method of claim 3, wherein said nucleic acid encoding a glycolate dehydrogenase multi-subunit fusion protein comprises the polynucleotide sequences of SEQ ID NO: 1, 3, and 5.

15. The nucleic acid of claim 4, wherein said glycolate dehydrogenase multi-subunit fusion protein comprises the amino acid sequences of SEQ ID NO: 2, 4, and 6.

16. The nucleic acid of claim 6, wherein said nucleic acid encoding a glycolate dehydrogenase multi-subunit fusion protein comprises the polynucleotide sequences of SEQ ID NO: 1, 3, and 5.

17. A transgenic plant cell comprising a nucleic acid encoding a glycolate dehydrogenase multi-subunit fusion protein of claim 15.

18. A transgenic plant, and part thereof, comprising a transgenic plant cell according to claim 17.

19. A transgenic plant, and part thereof, according to claim 18 selected among rice, wheat, barley, potato, rapeseed, tobacco.

20. A transgenic seed comprising a transgenic plant cell according to claim 17.

21. A transgenic seed according to claim 20 selected from the group consisting of rice, wheat, barley, rapeseed, and tobacco.

* * * * *